(12) United States Patent
Wang

(10) Patent No.: US 9,809,857 B2
(45) Date of Patent: Nov. 7, 2017

(54) METHODS AND SIGNATURES FOR OROPHARYNGEAL CANCER PROGNOSIS

(71) Applicant: The Washington University, St. Louis, MO (US)

(72) Inventor: Xiaowei Wang, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 73 days.

(21) Appl. No.: 14/193,975

(22) Filed: Feb. 28, 2014

(65) Prior Publication Data

US 2014/0243219 A1 Aug. 28, 2014

Related U.S. Application Data

(60) Provisional application No. 61/770,730, filed on Feb. 28, 2013.

(51) Int. Cl.
*C12Q 1/68* (2006.01)

(52) U.S. Cl.
CPC ...... *C12Q 1/6886* (2013.01); *C12Q 2600/112* (2013.01)

(58) Field of Classification Search
None
See application file for complete search history.

(56) References Cited

PUBLICATIONS

Ambros, "The functions of animal microRNAs", Nature, 2004, pp. 350-355, vol. 431.
Ang et al., "Human Papillomavirus and Survival of Patients with Oropharyngeal Cancer", N Engl J Med., 2010, pp. 24-35, vol. 363, No. 1.
Avissar et al., "A MicroRNA Expression Ratio is Predictive of Head and Neck Squamous Cell Carcinoma", Clin Cancer Res., 2009; pp. 2850-2855, vol. 15, No. 8.
Calin et al., "MicroRNA signatures in human cancers", Nat Rev Cancer, 2006, pp. 857-866, vol. 6.
Chernock et al., "HPV-Related Nonkeratinizing Squamous Cell Carcinoma of the Oropharynx: Utility of Microscopic Features in Predicting Patient Outcome", Head and Neck Pathol., 2009, pp. 186-194, vol. 3.
Childs et al., "Low-Level Expression of MicroRNAs let-7d and miR-205 Are Prognostic Markers of Head and Neck Squamous Cell Carcinoma", Am J Pathol., 2009, pp. 736-745, vol. 174, No. 3.
D'Souza et al., "Case-Control Study of Human Papillomavirus and Oropharyngeal Cancer", N Engl J Med., 2007, pp. 1944-1956, vol. 356, No. 19.
D'Souza et al., "Oral Sexual Behaviors Associated with Prevalent Oral Human Papillomavirus Infection", J Infect Dis., 2009, pp. 1263-1269, vol. 199.
Ernster et al., "Rising Incidence of Oropharyngeal Cancer and the Role of Oncogenic Human Papilloma Virus", Laryngoscope, 2007, pp. 2115-2128, vol. 117.
Fakhry et al., "Improved Survival of Patients With Human Papillomavirus-Positive Head and Neck Squamous Cell Carcinoma in a Prospective Clinical Trial", J Natl Cancer Inst., 2008, pp. 261-269, vol. 100, No. 4.
Frank et al., "Data mining in bioinformatics using Weka", Bioinformatics, 2004, pp. 2479-2481, vol. 20, No. 15.
Gao et al., "A microRNA expression signature for the prognosis of oropharyngeal squamous cell carcinoma", Cancer, 2013, pp. 72-80, vol. 119, No. 1.
Gao et al., "A novel RT-PCR method for quantification of human papillomavirus transcripts in archived tissues and its application in oropharyngeal cancer prognosis", Int J Cancer, 2013, pp. 882-890, vol. 132, No. 4.
Gillison et al., "Distinct Risk Factor Profiles for Human Papillomavirus Type 16-Positive and Human Papillomavirus Type 16-Negative Head and Neck Cancers", J Natl Cancer Inst., 2008, pp. 407-420, vol. 100. No. 6.
Hu et al., "A MicroRNA Expression Signature for Cervical Cancer Prognosis", Cancer Res., 2010, pp. 1441-1448, vol. 70, No. 4.
Hui et al. "Comprehensive Micro-RNA Profiling for Head and Neck Squamous Cell Carcinomas", Clin Cancer Res., 2010, pp. 1129-1139, vol. 16, No. 4.
Hurst et al., "Breast Cancer Metastasis Suppressor 1 Up-regulates miR-146, Which Suppresses Breast Cancer Metastasis", Cancer Res., 2009, pp. 1279-1283, vol. 69, No. 4.
Jay et al., "miRNA Profiling for Diagnosis and Prognosis of Human Cancer", DNA Cell Biol., 2007, pp. 293-300, vol. 26, No. 5.
Jazdzewski et al., "Common SNP in pre-miR-146a decreases mature miR expression and predisposes to papillary thyroid carcinoma", Proc Natl Acad Sci USA, 2008, pp. 7269-7274, vol. 105, No. 20.
Johnson et al., "The let-7 Micro-RNA Represses Cell Proliferation Pathways in Human Cells", Cancer Res., 2007, pp. 7713-7722, vol. 67, No. 16.
Kent et al., "A small piece in the cancer puzzle: microRNAs as tumor suppressors and oncogenes", Oncogene, 2006, pp. 6188-6196, vol. 25.
Kogo et al., "Clinical Significance of miR-146a in Gastric Cancer Cases", Clin Cancer Res., 2011, pp. 4277-4284, vol. 17, No. 13.
Lajer et al., "Different miRNA signatures of oral and pharyngeal squamous cell carcinomas: a prospective translational study", Br J Cancer, 2011, pp. 830-840, vol. 104, No. 5.
Lewis et al., "Conserved Seed Pairing, Often Flanked by Adenosines, Indicates that Thousands of Human Genes are MicroRNA Targets", Cell, 2005, pp. 15-20, vol. 120.
Lewis et al., "p16 Positive Oropharyngeal Squamous Cell Carcinoma: An Entity With a Favorable Prognosis Regardless of Tumor HPV Status", Am J Surg Pathol., 2010, pp. 1088-1096, vol. 34, No. 8.
Li et al., "miR-146a Suppresses Invasion of Pancreatic Cancer Cells", Cancer Res., 2010, pp. 1486-1495, vol. 70, No. 4.

(Continued)

*Primary Examiner* — Antonio Galisteo Gonzalez
(74) *Attorney, Agent, or Firm* — Polsinelli PC

(57) ABSTRACT

Methods for determining the prognosis of a subject with oropharyngeal squamous cell carcinoma are described, as well as miRNAs and panels of prognostic miRNAs that are used in the methods.

18 Claims, 7 Drawing Sheets
(3 of 7 Drawing Sheet(s) Filed in Color)

(56) References Cited

PUBLICATIONS

Licitra et al., "High-Risk Human Papillomavirus Affects Prognosis in Patients With Surgically Treated Oropharyngeal Squamous Cell Carcinoma", J Clin Oncol., 2006, pp. 5630-5636, vol. 24, No. 36.

Lim et al., "Microarray analysis shows that some microRNAs downregulate large numbers of target mRNAs", Nature, 2005, pp. 769-773, vol. 433.

Liu et al., "miR-31 Ablates Expression of the HIF Regulatory Factor FIH to Activate the HIF Pathway in Head and Neck Carcinoma", Cancer Res., 2010, pp. 1635-1644, vol. 70, No. 4.

Liu et al., "MicroRNA-24 targeting RNA-binding protein DND1 in tongue squamous cell carcinoma", FEBS Lett., 2010, pp. 4115-4120, vol. 584, No. 18.

Liu et al., "Exploiting Salivary miR-31 as a Clinical Biomarker of Oral Squamous Cell Carcinoma", Head Neck, 2012, pp. 219-224, vol. 34.

Miranda et al., "A Pattern-Based Method for the Identification of MicroRNA Binding Sites and Their Corresponding Heteroduplexes", Cell, 2006, pp. 1203-1217, vol. 126.

Miska, "How microRNAs control cell division, differentiation and death", Curr Opin Genet Dev., 2005, pp. 563-568, vol. 15.

Reiner et al., "Identifying differentially expressed genes using false discovery rate controlling procedures", Bioinformatics, 2003, pp. 368-375, vol. 19, No. 3.

Schouten et al., "Relative quantification of 40 nucleic acid sequences by multiplex ligation-dependent probe amplification", Nucl. Acids Res., 2002, e57, 13 pgs., vol. 30, No. 12.

Shi et al., "Comparative Prognostic Value of HPV16 E6 mRNA Compared With In Situ Hybridization for Human Oropharyngeal Squamous Carcinoma", J Clin Oncol., 2009, pp. 6213-6221, vol. 27, No. 36.

Syrjanen, "Human papillomavirus (HPV) in head and neck cancer", J Clin Virol., 2005, pp. S59-S66, vol. 32S.

Tran et al., "MicroRNA expression profiles in head and neck cancer cell lines", Biochem Biophys Res Commun., 2007, pp. 12-17, vol. 358.

Wald et al., "Human papillomavirus alters microRNA profiles in squamous cell carcinoma of the head and neck (SCCHN) cell lines", Head Neck, 2011, pp. 504-512, vol. 33, No. 4.

Wang et al., "A PCR primer bank for quantitative gene expression analysis", Nucleic Acids Res., 2003, p. e154, 8 pgs., vol. 31, No. 24.

Wang, "A PCR-based platform for microRNA expression profiling studies", RNA, 2009, pp. 716-723, vol. 15, No. 4.

Yu et al., "Unique MicroRNA Signature and Clinical Outcome of Cancers", DNA Cell Biol., 2007, pp. 283-292, vol. 26, No. 5.

Yu et al., "MicroRNA Signature Predicts Survival and Relapse in Lung Cancer", Cancer Cell., 2008, pp. 48-57, vol. 13.

Zhang et al., "Ramification Amplification: A Novel Isothermal DNA Amplification Method", Molecular Diagnosis, pp. 141-150, vol. 6, No. 2.

METHODS AND SIGNATURES FOR OROPHARYNGEAL CANCER PROGNOSIS

CROSS REFERENCE TO RELATED APPLICATIONS

This application claims the priority of U.S. provisional application No. 61/770,730, filed Feb. 28, 2013, which is hereby incorporated by reference in its entirety.

GOVERNMENTAL RIGHTS

This invention was made with government support under R01GM089784 awarded by the National Institutes of Health. The government has certain rights in the invention.

FIELD OF THE INVENTION

The invention describes novel panels of nucleic acids and methods of using them for determining the prognosis of a subject with oropharyngeal squamous cell carcinoma.

BACKGROUND OF THE INVENTION

Oropharyngeal cancer is a disease in which malignant cells form in the tissue of the oropharynx. The oropharynx is a part of the throat that includes the base of the tongue, the tonsils, the soft palate, and the walls of the pharynx. Oropharyngeal cancer has many unique characteristics that distinguish it from other types of head and neck cancer. For instance, oropharyngeal cancer has a strong association with human papillomavirus (HPV) infection. In addition, although the overall incidence of head and neck cancer has decreased steadily within the past decades, the number of reported cases of oropharyngeal cancer has increased significantly. Currently, oncologists rely primarily on the stage of the tumor to make treatment decisions for patients with oropharyngeal cancer. The HPV status of patients with oropharyngeal cancer has also been proposed as a promising prognostic marker and treatment factor. However, these methods either rely primarily on the early diagnosis of head and neck cancer, or fail to predict disease outcome of oropharyngeal cancer. Predicting disease outcome of patients with oropharyngeal cancer may improve patient outcomes by identifying patients who are likely to fail standard therapy and who could potentially benefit from alternative or targeted treatments. Therefore, there is an urgent need for a method to predict disease outcome that focuses specifically on oropharyngeal cancer.

SUMMARY OF THE INVENTION

Accordingly, in one aspect, the present disclosure provides a method of identifying a subject with oropharyngeal cancer as having a poor or a favorable prognosis. The method comprises, obtaining a sample from the subject, and processing the sample, in vitro, to determine in the sample the levels of a panel of at least two prognostic miRNAs selected from the group consisting of miR-142-3p, miR-31, miR-146a, miR-26b, miR-24, miR-29b, miR-203, miR-155, miR-193b, miR-26a, miR-215, miR-101, let-7i, miR-9, miR-223, miR-155, and miR-18a. A risk score may then be calculated using the levels of miRNAs. The calculated risk score may be compared to a median risk score. If the risk score is equal to or higher than the median risk score, the subject has a poor prognosis, and if the risk score is lower than the median risk score, the subject has a favorable prognosis.

In another aspect, the present disclosure provides a method for determining the prognosis of a subject with oropharyngeal carcinoma. The method comprises measuring expression levels of at least two miRNAs chosen from miR-24, miR-31, miR-193b, miR-26b, miR-142-3p, and miR-146a. A risk score may then be calculated according to the following formula:

$$S = C_1E_1 + C_2E_2 + C_3E_3 - C_4E_4 - C_5E_5 - C_6E_6$$

wherein $C_1$, $C_2$, $C_3$, $C_4$, $C_5$, and $C_6$ are coefficients, $E_1$ is the expression level of miR-24, $E_2$ is the expression level of miR-31, $E_3$ is the expression level of miR-193b, $E_4$ is the expression level of miR-26b, $E_5$ is the expression level of miR-142-3p; and $E_6$ is the expression level of miR-146a. Prognosis may be assessed by comparing the risk score to a median risk score.

In yet another aspect, the present disclosure provides a kit for determining the prognosis of a subject with oropharyngeal carcinoma. The kit may comprise at least two probes, each probe being specific for a miRNA in a panel of prognostic miRNAs selected from the group consisting of miR-142-3p, miR-31, miR-146a, miR-26b, miR-24, miR-29b, miR-203, miR-155, miR-193b, miR-26a, miR-215, miR-101, let-7i, miR-9, miR-223, miR-155, and miR-18a.

BRIEF DESCRIPTION OF THE FIGURES

The application file contains at least one drawing executed in color. Copies of this patent application publication with color drawing(s) will be provided by the Office upon request and payment of the necessary fee.

DETAILED DESCRIPTION OF THE INVENTION

Figure 1:
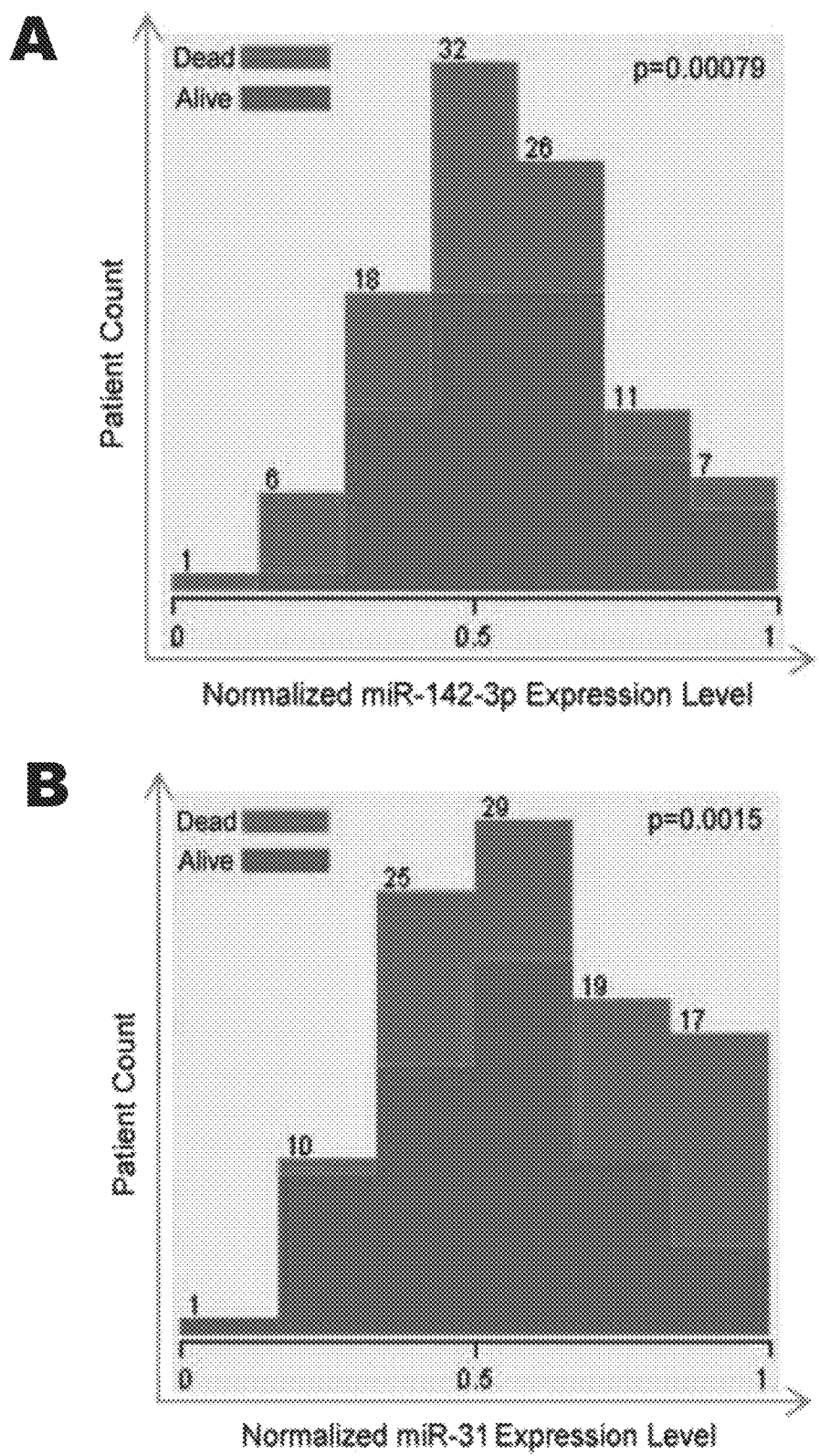
FIG. 1 (A-F) depicts six plots showing the expression profiles of six prognostic microRNAs (miRNAs) in 101 patients with oropharyngeal squamous cell carcinomas. (A) miR-142-3p; (B) miR-31; (C) miR-146a; (D) miR-26b; (E) miR-24; and (F) miR-193b. The patients were stratified into 2 groups according to their survival status (deceased or alive). The expression profiles of individual miRNAs were determined in each group, and were normalized using a quantile-based scaling method as described in Wang et al., 2009 RNA 15:716-723. The normalized expression data were observed by further scaling to the value range of 0 to 1 and grouped into multiple bins with Weka (Waikato Environment for Knowledge Analysis) software. The P values were calculated using the Wald test in univariate Cox regression analysis, and further adjusted with permutation tests.
Figure 1:
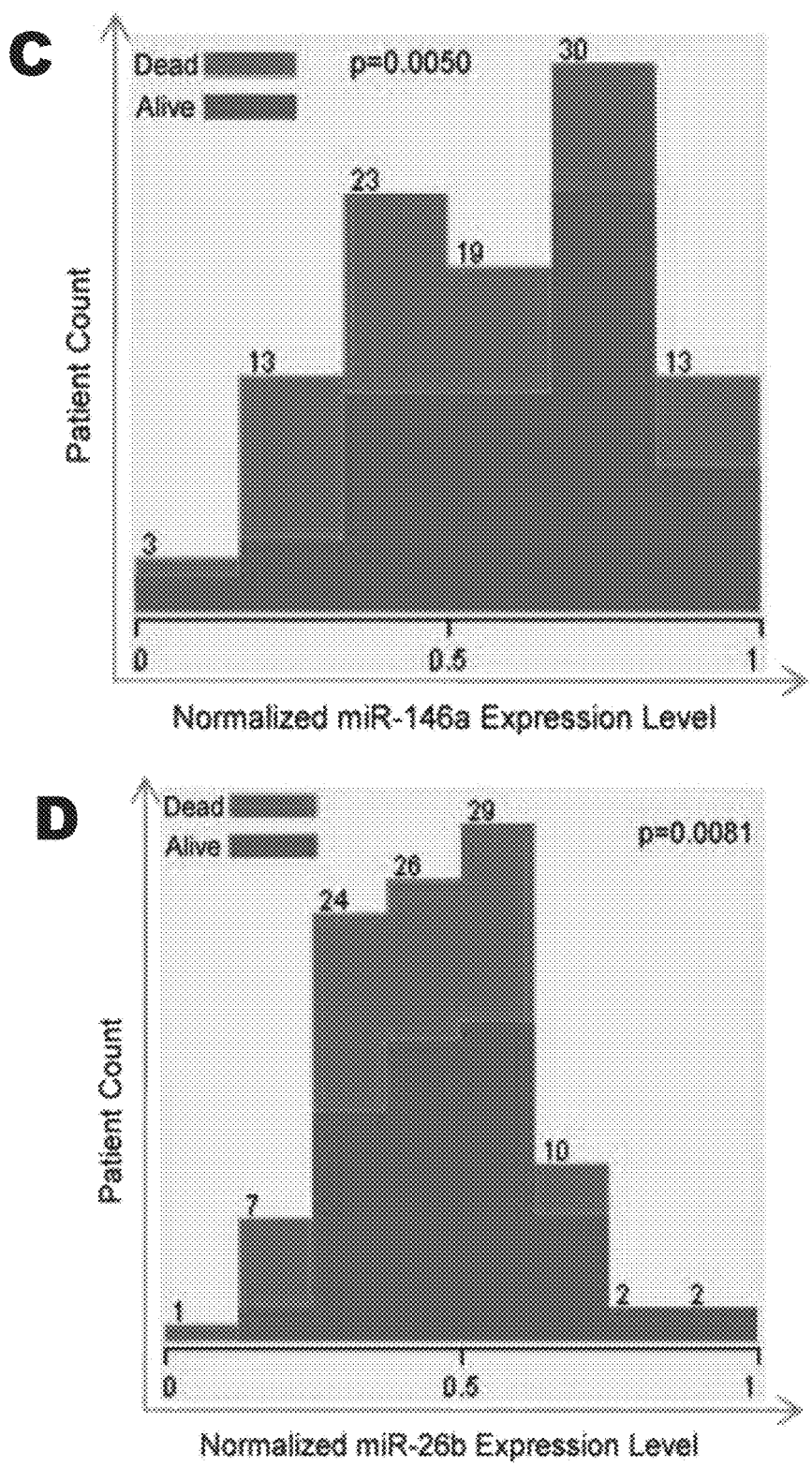
Figure 1:
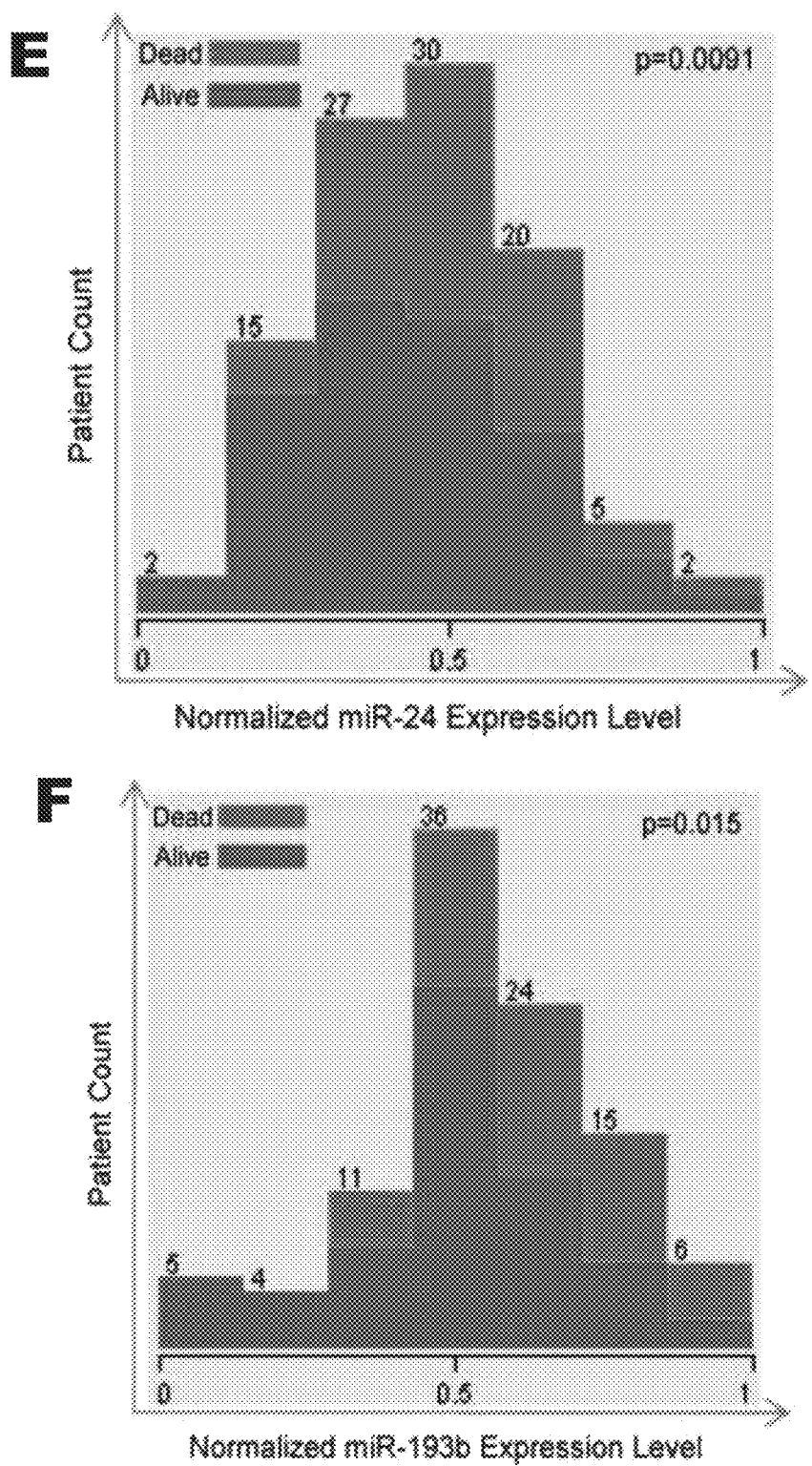

The present disclosure provides a method for identifying a subject with oropharyngeal cancer as having a poor or a favorable prognosis. Oropharyngeal cancer may be any cancer disease formed in the oropharynx, i.e., the middle part of the throat, including the base of the tongue, the tonsils, the soft palate, and the walls of the pharynx. For example, oropharyngeal cancer includes but is not limited to oropharyngeal squamous cell carcinoma.

Determining the prognosis of a subject with an oropharyngeal cancer such as squamous cell carcinoma using a method as described herein may improve patient outcome by identifying subjects who are likely to fail standard therapy and who could potentially benefit from alternative or targeted treatments. Advantageously, such a method may allow a physician to determine the severity of an oncogenic disease in a subject and to make appropriate, informed, and timely treatment decisions based on this information. The present disclosure also provides a panel of prognostic miRNAs for identifying a subject with oropharyngeal cancer as having a poor or a favorable prognosis.

I. Methods

The present disclosure encompasses a method for identifying a subject with oropharyngeal cancer as having a poor or a favorable prognosis. The method comprises obtaining a sample from a subject, and processing the sample to determine the expression levels of one or more miRNA in a panel of prognostic miRNAs, as described herein. The levels of miRNAs may be used to calculate a risk score for the subject. When compared to a median risk score, the calculated risk score may be used to identify a subject with oropharyngeal cancer as having a poor or favorable prognosis.

(a) Panel of Prognostic miRNAs

The methods described herein comprise determining the expression levels of one or more miRNAs in a panel of prognostic miRNAs. As used herein, the term "miRNA" refers to a small (e.g. generally less than 30 nucleotides) non-coding RNA molecule which functions in transcriptional and post-transcriptional regulation of gene expression. A miRNA functions via base-pairing with complementary sequences within mRNA molecules, usually resulting in gene silencing via translational repression or target degradation. A mature miRNA is processed through a series of steps from a larger primary RNA transcript (pri-miRNA), or from an intron comprising a miRNA (mirtron), to generate a stem loop pre-miRNA structure comprising the miRNA sequence. A pre-miRNA is then cleaved to generate the mature miRNA. A miRNA may be a pri-miRNA, a pre-miRNA, or a mature miRNA. A miRNA may also be a mirtron miRNA. In non-limiting examples, the miRNA is a mature miRNA.

A panel of prognostic miRNAs may include miRNAs whose level of expression is related to disease outcome of oropharyngeal cancer. miRNAs having such a level of expression may include miR-142-3p, miR-31, miR-146a, miR-26b, miR-24, miR-29b, miR-203, miR-155, miR-193b, miR-26a, miR-215, miR-101, let-7i, miR-9, miR-223, miR-155, and miR-18a. A panel of prognostic miRNAs may include any miRNA having a level of expression that may be correlated with disease outcome of oropharyngeal cancer.

In general, a miRNA in a panel of prognostic miRNAs has a level of expression correlated with disease outcome. As used herein, the term "disease outcome" is used to describe the survival of a subject with oropharyngeal cancer. Disease outcome may be overall survival of a subject with oropharyngeal cancer, and may represent the time interval between treatment start date, and the date of death of a subject from any cause. Alternatively, disease outcome may be disease-specific survival of a subject with oropharyngeal cancer, and may represent the time interval between treatment start date, and the date of death of a subject with cancer disease. In yet another alternative, disease outcome may refer to metastasis-specific survival.

A miRNA having a level of expression correlated with oropharyngeal cancer disease outcome may have decreased miRNA levels in a sample of oropharyngeal cancer, wherein the decreased level of the miRNA is correlated with disease outcome. Alternatively, a miRNA having a level of expression correlated with oropharyngeal cancer survival may have increased miRNA levels in a sample of oropharyngeal cancer, wherein the increased level of the miRNA is correlated with disease outcome. According to the disclosure, a miRNA having a level of expression correlated with oropharyngeal cancer disease outcome has decreased or increased miRNA levels in a sample of oropharyngeal cancer.

Methods of determining correlation of the level of a miRNA with disease outcome are known in the art and may include statistical analysis methods capable of determining a correlation between the level of a miRNA and disease outcome. For instance, correlation of the level of a miRNA with disease outcome may be determined using survival analysis methods such as univariate Cox proportional hazards regression analysis, and multivariate Cox proportional hazards regression analysis. Preferably, correlation of the expression level of a miRNA with disease outcome may be determined using statistical analysis methods known in the art, and may be as described in the Examples.

A miRNA having a level of expression that may be correlated with disease outcome of oropharyngeal cancer may be used to identify a subject with oropharyngeal cancer as having a poor or a favorable prognosis. However, it should be understood by those of skill in the art, that a panel of prognostic miRNAs comprising more than one miRNA may provide a more accurate prognosis. As such, a panel of prognostic miRNAs may comprise at least two miRNAs. For instance, a panel of prognostic miRNAs may comprise 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100 or more miRNAs. A panel of prognostic miRNAs may comprise 2, 3, 4, or 5 miRNAs, 5, 6, 7, 8, 9, or 10 miRNAs, 10, 11, 12, 13, 14, or 15 miRNAs, 15, 16, 17, 18, 19, or 20 miRNAs, 20, 21, 22, 23, 24, 25, or more miRNAs. Preferably, a panel of prognostic miRNAs comprises 5, 6, 7, 8, 9, or 10 miRNAs.

A panel of prognostic miRNAs may comprise at least two miRNAs selected from the group of miRNAs consisting of miR-142-3p, miR-31, miR-146a, miR-26b, miR-24, miR- 29b, miR-203, miR-155, miR-193b, miR-26a, miR-215, miR-101, let-7i, miR-9, miR-223, miR-155, and miR-18a.

Preferably, a panel of prognostic miRNAs may comprise at least six miRNAs selected from the group of miRNAs consisting of miR-142-3p, miR-31, miR-146a, miR-26b, miR-24, miR-29b, miR-203, miR-155, miR-193b, miR-26a, miR-215, miR-101, let-7i, miR-9, miR-223, miR-155, and miR-18a. An exemplary panel of prognostic miRNAs consists of miR-142-3p, miR-31, miR-146a, miR-26b, miR-24, and miR-193b.

A panel of prognostic miRNAs may also comprise at least five miRNAs selected from the group of miRNAs consisting of miR-142-3p, miR-31, miR-146a, miR-26b, miR-24, miR-29b, miR-203, miR-155, miR-193b, miR-26a, miR-215, miR-101, let-7i, miR-9, miR-223, miR-155, and miR-18a. An exemplary panel of prognostic miRNAs consists of miR-31, miR-9, miR-223, miR-155, and miR-18a.

A panel of prognostic miRNAs may comprise at least ten miRNAs selected from the group of miRNAs consisting of miR-142-3p, miR-31, miR-146a, miR-26b, miR-24, miR-29b, miR-203, miR-155, miR-193b, miR-26a, miR-215, miR-101, let-7i, miR-9, miR-223, miR-155, and miR-18a. An exemplary panel of prognostic miRNAs consists of miR-142-3p, miR-31, miR-146a, miR-26b, miR-24, miR-193b, miR-9, miR-223, miR-155, and miR-18a.

(b) Determining the Expression Level of a miRNA

A sample is processed to determine the expression levels of miRNAs in a panel of prognostic miRNAs. A sample may be obtained and prepared for processing as described in Section I(d).

Methods of determining the level of a miRNA are known and commonly used in the art. Non limiting examples of methods that may be used to determine the levels of a miRNA include cloning, northern analysis, primer extension, an array, PCR, sequencing, and combinations thereof. The levels of prognostic miRNAs may be determined using cloning. For instance, miRNAs may be cloned from a sample, and the cloned miRNAs sequenced to determine expression levels of miRNAs. Alternatively, the levels of prognostic miRNAs may be determined by northern analysis. Methods of determining levels of miRNAs using northern analysis are known in the art. The levels of prognostic miRNAs may also be determined by primer extension. Methods of determining expression levels of miRNAs using primer extension are known in the art. The levels of prognostic miRNAs may also be determined by an array. Methods of determining levels of miRNAs using an array are known in the art. In addition, the levels of prognostic miRNAs may be determined by sequencing. For instance, high throughput sequencing methods modified for sequencing small RNAs may be used to determine the levels of miRNAs. High throughput sequencing of miRNAs generates millions of reads from a given sample, such that the levels of miRNAs in a sample may be determined. Non limiting examples of high throughput sequencing methods that may be used to determine the levels of miRNAs include pyrosequencing, polymerase-based sequence-by-synthesis, and sequencing by ligation.

Preferably, the expression levels of prognostic miRNAs are determined by amplification techniques. Non-limiting examples of amplification techniques may include polymerase chain reaction, ligase chain reaction, nucleic acid sequence based amplification (NASBA), strand displacement amplification (SDA), transcription mediated amplification (TMA), loop-mediated isothermal amplification (LAMP), Q-beta replicase, rolling circle amplification, 3SR, ramification amplification (Zhang et al. (2001) Molecular Diagnosis 6 p 141-150), multiplex ligation-dependent probe amplification (Schouten et al. (2002) Nucl. Ac. Res. 30 e57). A summary of many of these techniques may be found in "DNA Amplification: Current technologies and applications" (Eds. Demidov & Broude (2004) Pub. Horizon Bioscience, ISBN: 0-9545232-9-6) and other current textbooks.

Even more preferably, the levels of prognostic miRNAs are determined by polymerase chain reaction (PCR). Methods of determining miRNA expression levels using PCR are well and widely known in the art, and may include quantitative real time PCR, semi-quantitative PCR, multiplex PCR, or any combination thereof. Preferably, the levels of prognostic miRNAs are determined by quantitative real time PCR (RT-PCR).

Methods of determining the levels of miRNAs using RT-PCR are known in the art. RT-PCR of miRNAs is generally preceded by reverse transcription of a miRNA into a cDNA. The reverse transcription, the RT-PCR, or the reverse transcription and the RT-PCR may be multiplexed to determine the levels of prognostic miRNAs of the disclosure. According to the present disclosure, individual reverse transcription reactions may be used for each miRNA in a panel of prognostic miRNAs, and the RT-PCR is multiplexed. Alternatively, the reverse transcription, and the RT-PCR may be multiplexed.

Preferably, the reverse transcription is multiplexed, and individual RT-PCR reactions are used for each miRNA in a panel of prognostic miRNAs. Particularly, the levels of prognostic miRNAs are determined by RT-PCR as described in Wang 2009, RNA 15:716-723, which is incorporated herein by reference in its entirety. In this method, an RT-PCR of the disclosure is preceded by a multiplexed reverse transcription reaction using a pool of reverse transcription primers. These reverse transcription primers anneal specifically to the target miRNAs, leading to a pool of mixed cDNA products from the miRNAs of interest. Additionally, the reverse transcription primers anneal to the 3' end of the mature miRNA, and therefore, the primers specifically transcribe cDNAs of the mature miRNAs. After the RT reaction, individual RT-PCR reactions are performed to quantify the expression of an individual miRNA. Each RT-PCR is performed with two primers that are uniquely associated with the miRNA of interest, one with a miRNA-specific sequence and the other from the unique tag sequence in the RT primer. As such, these primers are not likely to cross-react to primers from other miRNA assays even though multiplexed reverse transcription reactions are performed. Preferably, the reverse transcription primers and the two RT-PCR primers specific for each prognostic miRNA may be as described in Wang et al., 2009 RNA 15:716-723, which is incorporated herein by reference in its entirety.

A method of the disclosure may determine an absolute level of expression of a prognostic miRNA. Alternatively, a method of the disclosure may determine the normalized level of a prognostic miRNA. Preferably, the absolute level of a prognostic miRNA is determined. Even more preferably, the normalized level of a prognostic miRNA is determined. The normalized level of a prognostic miRNA may be determined by normalizing the level of the miRNA to the level of one or more internal standard nucleic acid sequences. In general, such internal standard nucleic acid sequences should have a constant expression in a tumor sample, regardless of the disease outcome of the subject. For instance, internal standard nucleic acid sequences may be RNAs for housekeeping nucleic acid sequences such as mRNAs for the housekeeping genes glyceraldehyde-3-phosphate-dehydrogenase (GAPDH), beta-actin, or 18S rRNA, or miRNAs that have constant and high expression in a sample.

Preferably, the relative level of a prognostic miRNA is determined by normalizing to the level of one or more miRNAs that have constant and high expression in a sample, regardless of the disease outcome of the subject. For instance, the relative level of a prognostic miRNA may be determined by normalizing to the level of 1, 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100 or more miRNAs that have constant and high expression in a sample.

The relative level of a prognostic miRNA may be determined by normalizing to the level of 1, 2, 3, 4, 5, 6, 7, 8, 9, or 10 miRNAs. Preferably, the relative level of a prognostic miRNA may be determined by normalizing to the level of 10, 11, 12, 13, 14, 15, 16, 17, 18, 19, or 20 miRNAs, to the level of 20, 21, 22, 23, 24, 25, 30, 40, or 50 miRNAs, to the level of 50, 60, 70, 80, 90, 100 or more miRNAs, or preferably to the level of eight miRNAs.

The level of a prognostic miRNA of the disclosure may be increased or decreased as described in Section I(a). The increased or decreased level of a prognostic miRNA may be an increased or decreased level of miRNA levels when compared to an average level of the miRNA in samples from a population of subjects having oropharyngeal cancer. An exemplary population of subjects having oropharyngeal cancer may be as described in Table 1. An exemplary increase or decrease of the level of prognostic miRNA may be expressed as a $\log_2$ transformation of miRNA levels determined as described above and in the Examples. The level of a prognostic miRNA may be increased or decreased by about 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, or about 2.5 fold or more, when expressed as a $\log_2$ transformation of miRNA levels.

(c) Determining Prognosis

A method of the disclosure comprises determining if a subject with oropharyngeal cancer has a poor or favorable prognosis. Determining if a subject with oropharyngeal cancer has a poor or favorable prognosis may comprise calculating a risk score. A risk score may be calculated using the expression signatures of miRNAs in a panel of prognostic miRNAs. An expression signature of a miRNA may be determined using the normalized level of expression of the miRNA in a sample, and an independent prognostic value of the miRNA based on the correlation of the expression of the miRNA with disease outcome. Methods of determining an expression signature for a miRNA may be as described in the Examples. After determining the expression signatures of individual miRNAs in a panel of prognostic miRNAs, a risk score may be calculated by combining the expression signatures of each miRNA in a panel of prognostic miRNAs. Methods of calculating a risk score may be as described in the Examples. Prognostic miRNAs and panels of prognostic miRNAs may be as described in Section I(a). Normalized expression levels of individual miRNAs from each tumor may be as described in Section I(b).

Typically a risk score may be calculated according to the formula:

$$\sum_{n=1}^{k} S = (CE)_k$$

wherein C is a coefficient, E represents the normalized expression level of individual miRNAs, and k may be an integer from 1-100. Prognosis may be assessed by comparing the risk score to a median risk score.

The coefficient (C) for each miRNA may be the Z score from the Cox regression analysis, defined as Z=(Cox regression coefficient)/(standard error of the coefficient). Cox regression analysis is performed as described in Section I(a).

E represents the normalized expression level of at least 1 miRNA. The normalized expression level of individual miRNAs may be as described in Section I(b).

(CE) may be a positive or a negative value. If a miRNA is preferentially expressed in patients with a favorable prognosis, then the value may be positive. If a miRNA is preferentially expressed in patients with a poor prognosis, then the value may be negative.

k is an integer from 1 to 100. For example, k may be 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100 or greater. For example, k may be 2, 3, 4, or 5, or k may be 5, 6, 7, 8, 9, or 10, or k may be 10, 11, 12, 13, 14, or 15, or k may be 15, 16, 17, 18, 19, or 20, or k may be 20, 21, 22, 23, 24, 25, or greater. Preferably, k may be 5, 6, 7, 8, 9, or 10.

In an embodiment, a risk score may be calculated according to the following formula:

$$S=(C_1E_1)+(C_2E_2)+(C_3E_3)+(C_4E_4)+(C_5E_5)+(C_6E_6)$$

wherein $C_1$, $C_2$, $C_3$, $C_4$, $C_5$, and $C_6$ are coefficients, and $E_1$, $E_2$, $E_3$, $E_4$, $E_5$, and $E_6$ are the expression level of individual miRNAs as described above. Prognosis may be assessed by comparing the risk score to a median risk score.

In an exemplary embodiment, a risk score may be calculated according to the following formula:

$$S=C_1E_1+C_2E_2+C_3E_3-C_4E_4-C_5E_5-C_6E_6$$

wherein $C_1$, $C_2$, $C_3$, $C_4$, $C_5$, and $C_6$ are coefficients, $E_1$ is the expression level of miR-24, $E_2$ is the expression level of miR-31, $E_3$ is the expression level of miR-193b, $E_4$ is the expression level of miR-26b, $E_5$ is the expression level of miR-142-3p; and $E_6$ is the expression level of miR-146a. Prognosis may be assessed by comparing the risk score to a median risk score.

In some embodiments, a risk score may be calculated using the expression signatures of miRNAs of a panel of prognostic miRNAs comprising at least one miRNA selected from the group of miRNAs consisting of miR-142-3p, miR-31, miR-146a, miR-26b, miR-24, miR-29b, miR-203, miR-155, miR-193b, miR-26a, miR-215, miR-101, let-7i, miR-9, miR-223, miR-155, and miR-18a.

Preferably, a risk score may be calculated using the expression signatures of miRNAs of a panel of prognostic miRNAs comprising at least two prognostic miRNAs selected from the group of miRNAs consisting of miR-142-3p, miR-31, miR-146a, miR-26b, miR-24, miR-29b, miR-203, miR-155, miR-193b, miR-26a, miR-215, miR-101, let-7i, miR-9, miR-223, miR-155, and miR-18a, or more preferably using the expression signatures of miRNAs of a panel of prognostic miRNAs consisting of miR-142-3p, miR-31, miR-146a, miR-26b, miR-24, and miR-193b. For example, a panel of prognostic miRNAs may comprise at least 2, 3, 4, 5 or 6 prognostic miRNAs selected from the group of miRNAs consisting of miR-142-3p, miR-31, miR-146a, miR-26b, miR-24, miR-29b, miR-203, miR-155, miR-193b, miR-26a, miR-215, miR-101, let-7i, miR-9, miR-223, miR-155, and miR-18a, or a panel of prognostic miRNAs may comprise at least 2, 3, 4, 5 or 6 prognostic miRNAs selected from the group consisting of miR-142-3p, miR-31, miR-146a, miR-26b, miR-24, and miR-193b.

Also preferably, a risk score may be calculated using the expression signatures of miRNAs of a panel of prognostic miRNAs comprising at least five prognostic miRNAs selected from the group of miRNAs consisting of miR-142-3p, miR-31, miR-146a, miR-26b, miR-24, miR-29b, miR-203, miR-155, miR-193b, miR-26a, miR-215, miR-101, let-7i, miR-9, miR-223, miR-155, and miR-18a, and even more preferably using the expression signatures of miRNAs of a panel of prognostic miRNAs consisting of miR-31, miR-9, miR-223, miR-155, and miR-18a.

Also preferably, a risk score is calculated using the expression signatures of miRNAs of a panel of prognostic miRNAs comprising at least ten prognostic miRNAs selected from the group of miRNAs consisting of miR-142-3p, miR-31, miR-146a, miR-26b, miR-24, miR-29b, miR-203, miR-155, miR-193b, miR-26a, miR-215, miR-101, let-7i, miR-9, miR-223, miR-155, and miR-18a, more preferably using the expression signatures of miRNAs of a panel of prognostic miRNAs consisting of miR-142-3p, miR-31, miR-146a, miR-26b, miR-24, miR-193b, miR-9, miR-223, miR-155, and miR-18a, and even more preferably using the expression signatures of miRNAs of a panel of prognostic miRNAs consisting of miR-142-3p, miR-31, miR-146a, miR-26b, miR-24, and miR-193b as described in Example 2.

A calculated risk score of the disclosure may be used to determine the prognosis of a subject with oropharyngeal cancer. In general, a calculated risk score may be compared to a median risk score to determine the prognosis of a subject. If the risk score is equal to or higher than the median risk score, the subject has a poor prognosis. Alternatively, if the risk score is lower than the median risk score, the subject has a favorable prognosis. A median risk score may be the median of the risk scores calculated for each subject in a population of subjects with oropharyngeal cancer. Preferably, a median risk score may be the median of the risk scores calculated for each subject in a population of subjects described in Table 1.

Prognosis may be used to describe the risk of death of a subject with oropharyngeal cancer over time. For instance, prognosis may be used to describe the risk of death of a subject with oropharyngeal squamous cell carcinoma from the time of diagnosis. If a subject has a poor prognosis, the risk of death may be greater than about 30%, 35%, 40%, 45%, 50%, 55%, 60%, 65%, 70%, 75%, 80%, 85%, 90%, or about 95% one year from the time of diagnosis, about 35%, 40%, 45%, 50%, 55%, 60%, 65%, 70%, 75%, 80%, 85%, 90%, or about 95% two years year from the time of diagnosis, about 40%, 45%, 50%, 55%, 60%, 65%, 70%, 75%, 80%, 85%, 90%, or about 95% three years year from the time of diagnosis, about 45%, 50%, 55%, 60%, 65%, 70%, 75%, 80%, 85%, 90%, or about 95% four years year from the time of diagnosis, about 50%, 55%, 60%, 65%, 70%, 75%, 80%, 85%, 90%, or about 95% five years from the time of diagnosis, about 55%, 60%, 65%, 70%, 75%, 80%, 85%, 90%, or about 95% six years from the time of diagnosis, about 60%, 65%, 70%, 75%, 80%, 85%, 90%, or about 95% seven years from the time of diagnosis, about 65%, 70%, 75%, 80%, 85%, 90%, or about 95% eight years from the time of diagnosis, about 70%, 75%, 80%, 85%, 90%, or about 95% nine years from the time of diagnosis, or about 95% ten years from the time of diagnosis.

Conversely, If a subject has a favorable prognosis, the risk of death may be less than about 50% one year from the time of diagnosis, about 50%, or about 55% two years year from the time of diagnosis, about 50%, 55%, 60%, or about 65% three years year from the time of diagnosis, about 50%, 55%, 60%, 65%, or about 70% four years year from the time of diagnosis, about 50%, 55%, 60%, 65%, 70%, or about 75% five years from the time of diagnosis, about 50%, 55%, 60%, 65%, 70%, 75%, or about 80% six years from the time of diagnosis, about 50%, 55%, 60%, 65%, 70%, 75%, 80%, or about 85% seven years from the time of diagnosis, about 50%, 55%, 60%, 65%, 70%, 75%, 80%, or about 85% eight years from the time of diagnosis, about 50%, 55%, 60%, 65%, 70%, 75%, 80%, 85%, or about 90% nine years from the time of diagnosis, or about 50%, 55%, 60%, 65%, 70%, 75%, 80%, 85%, 90%, or about 95% ten years from the time of diagnosis.

A method of the disclosure may also be used in combination with other methods of oropharyngeal cancer diagnosis or prognosis for determining if a subject with oropharyngeal cancer has a poor or favorable prognosis. Non limiting examples of methods of oropharyngeal cancer diagnosis or prognosis that may be used with a method of the disclosure may include clinicopathological methods such as cytological analysis of a cancer sample, and the HPV status of a cancer sample. Preferably, a method of the disclosure is used in combination with clinicopathological analysis, and even more preferably, a method of the disclosure is used in combination with the HPV status of a cancer sample. In general, if a cancer sample is infected with HPV, a subject has a favorable prognosis. Conversely, if a cancer sample is not infected with HPV, a subject has a poor prognosis.

(d) Obtaining a Sample from a Subject

A method of the disclosure comprises, in part, obtaining a sample from a subject. A sample of the disclosure may be obtained by freshly collecting a sample, or may be obtained from a previously collected and stored sample. For instance, a sample may be obtained from a collection of fixed tumor samples. Preferably, a sample is obtained by freshly collecting a sample. Also preferably, a sample is obtained from a previously collected and stored sample.

Suitable samples comprise one or more tumor cells, either from a primary tumor or a metastasis. A suitable sample may be a circulating tumor cell. Circulating tumor cells may be found in a bodily fluid (e.g., plasma, sputum, urine, etc.) or other excrement (e.g., feces). Preferably, a suitable sample comprises an oropharyngeal cancer cell, and even more preferably, an oropharyngeal squamous cell carcinoma cell.

Methods of obtaining tumor samples are well known in the art. For instance, a tumor sample may be obtained from a surgically resected tumor. Alternatively, the tumor sample may be obtained from a biopsy. This is advantageous when the tumor is small enough to not require resection. The tumor sample may be obtained from a fine needle biopsy, also known as a needle aspiration biopsy (NAB), a fine needle aspiration cytology (FNAC), a fine needle aspiration biopsy (FNAB), or a fine needle aspiration (FNA). Preferably, a tumor region may be microdissected from a tumor sample from a subject. A tumor sample may be fresh or otherwise stored so as to reduce nucleic acid degradation. For instance, a tumor sample may be a fresh frozen tumor sample or a formalin-fixed paraffin embedded tumor sample.

A sample may comprise about five cells or less. For instance, a tumor sample may comprise about 1, 2, 3, 4, 5, 6, 7, 8, 9, 10, 11, 12, 13, 14, 15 or more cells, or 20, 25, 30, 35, 40 or more cells.

II. Panel of Prognostic miRNAs for Prognosis

In another aspect, the present disclosure provides a panel of prognostic miRNAs for determining if a subject with oropharyngeal cancer has a poor or favorable prognosis. A panel of prognostic miRNAs of the disclosure may comprise at least two prognostic miRNAs selected from the group consisting of miR-142-3p, miR-31, miR-146a, miR-26b, miR-24, miR-29b, miR-203, miR-155, miR-193b, miR-26a, miR-215, miR-101, let-7i, miR-9, miR-223, miR-155, and miR-18a. Additionally, a panel of prognostic miRNAs may comprise at least 3, 4, 5, 6, 7, 8, 9, or 10 miRNAs selected from the group consisting of miR-142-3p, miR-31, miR-146a, miR-26b, miR-24, miR-29b, miR-203, miR-155, miR-193b, miR-26a, miR-215, miR-101, let-7i, miR-9, miR-223, miR-155, and miR-18a.

Panels of prognostic miRNAs, oropharyngeal cancer, and prognosis, may be as described in Section I above. The panel of prognostic miRNAs may consist of miR-142-3p, miR-31, miR-146a, miR-26b, miR-24, miR-193b, miR-9, miR-223, miR-155, and miR-18a, more preferably miR-31, miR-9, miR-223, miR-155, and miR-18a, and even more preferably miR-24, miR-31, miR-193b, miR-26b, miR-142-3p, and miR-146a.

III. Kit for Prognosis

In yet another aspect, the present disclosure provides a kit for determining the prognosis of a subject with oropharyngeal carcinoma. The kit may comprise at least two probes, each probe being specific for a miRNA in the panel of prognostic miRNAs selected from the group consisting of miR-142-3p, miR-31, miR-146a, miR-26b, miR-24, miR-29b, miR-203, miR-155, miR-193b, miR-26a, miR-215, miR-101, let-7i, miR-9, miR-223, miR-155, and miR-18a.

Panels of prognostic miRNAs, oropharyngeal cancer, and prognosis, may be as described in Section I above. The kit may comprise at least two probes, each probe being specific for a miRNA in the panel of prognostic miRNAs consisting of miR-142-3p, miR-31, miR-146a, miR-26b, miR-24, miR-193b, miR-9, miR-223, miR-155, and miR-18a, more preferably consisting of miR-31, miR-9, miR-223, miR-155, and miR-18a, and even more preferably consisting of miR-24, miR-31, miR-193b, miR-26b, miR-142-3p, and miR-146a. Each probe may be a set of specific primers, a labeled nucleic acid probe, or a specific antibody. Preferably, each probe may be a set of specific primers as described in Section I(b), and in Wang et al., 2009 RNA 15:716-723, which is incorporated herein by reference in its entirety. A kit may further comprise at least one reagent.

EXAMPLES

The following examples are included to demonstrate preferred embodiments of the disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Introduction for Examples 1-5

Unlike most other types of head and neck cancer, oropharyngeal squamous cell carcinoma (SCC) has many unique characteristics, including its strong association with human papillomavirus (HPV) infection. Epidemiologic studies have indicated that HPV-positive oropharyngeal cancer occurs commonly in patients who are of younger age and have a higher number of sexual partners, more exposure to oral sexual practices, and lower smoking rates. Previous studies have also shown that HPV-infected patients with oropharyngeal cancer generally have a more favorable outcome compared with those without HPV infection. However, the molecular mechanisms underlying this divergence in disease outcome are largely unknown.

Although the overall incidence of head and neck cancer has decreased steadily within the past decades, the number of reported cases of oropharyngeal cancer has increased significantly. Thus, there is an urgent need to focus specifically on oropharyngeal cancer to determine its unique characteristics with the goal of developing specific and targeted treatments. Currently, oncologists rely primarily on tumor stage to make treatment decisions for patients with oropharyngeal cancer. In recent years, the HPV status of patients with oropharyngeal cancer has also been proposed as a promising prognostic marker and treatment factor.

In the current study, we investigated the prognostic value of microRNAs (miRNAs) for oropharyngeal SCC. miRNAs are a family of small, noncoding RNAs that suppress the expression of their gene targets. Approximately 1000 human miRNAs have been identified to date. Both computational and experimental studies have indicated that thousands of human protein-coding genes are directly regulated by miRNAs. Thus, miRNAs function as master regulators for many important biological processes, including cell growth, apoptosis, viral infection, and cancer initiation and progression.

Previous studies have demonstrated that miRNA expression signatures are promising for the diagnosis and prognosis of a wide array of human cancers. However, the prognostic value of miRNAs in patients with oropharyngeal cancer has not been investigated to date. Specifically, miRNA studies focused primarily on the early diagnosis of head and neck cancer, but not the prediction of disease outcome. As a prediction of disease outcome can alter treatment decisions, a prognostic assay for oropharyngeal cancer is needed.

Materials and Methods for Examples 1-5

Patients and Tumor RNA Samples

A total of 150 oropharyngeal SCC cases were included in the current study, including 101 cases for training and 49 cases for validating a new miRNA-based prognostic model (Table 1). All the tumor tissues were collected from patients treated by a single radiation oncologist. All the patients were treated with either definitive radiotherapy or surgery followed by postoperative radiotherapy. In addition, approximately one-half of the patients also received chemotherapy. Clinical data were collected prospectively from the patients and were then updated retrospectively after follow-up review.

TABLE 1

Characteristics of the patients with oropharyngeal SCC[a]

| Characteristic | Training Cohort (n = 101) | Validation Cohort (n = 49) |
|---|---|---|
| Age at diagnosis (mean ± SD), y | 56.1 ± 9.1 | 56.2 ± 9.3 |
| Sex | | |
| Male | 94 (93%) | 43 (88%) |
| Female | 7 (7%) | 6 (12%) |
| Race | | |
| White | 85 (84%) | 46 (94%) |
| Other | 16 (16%) | 3 (6%) |
| Smoking[b] | | |
| Yes | 74 (74%) | 33 (67%) |
| No | 26 (26%) | 16 (33%) |

TABLE 1-continued

Characteristics of the patients with oropharyngeal SCC[a]

| Characteristic | Training Cohort (n = 101) | Validation Cohort (n = 49) |
|---|---|---|
| T classification | | |
| T1 | 25 (25%) | 7 (15%) |
| T2 | 38 (38%) | 17 (35%) |
| T3 | 13 (13%) | 12 (25%) |
| T4 | 24 (24%) | 12 (25%) |
| N classification | | |
| N0 | 7 (7%) | 4 (8%) |
| N1 | 15 (15%) | 6 (13%) |
| N2 | 71 (70%) | 37 (77%) |
| N3 | 8 (8%) | 1 (2%) |
| Histologic type | | |
| K SCC | 19 (19%) | 5 (10%) |
| NK SCC with maturation | 29 (29%) | 11 (22%) |
| NK SCC | 53 (52%) | 33 (67%) |

Abbreviations:
K SCC, keratinizing squamous cell carcinoma;
NK SCC, nonkeratinizing squamous cell carcinoma;
SD, standard deviation.
[a]The SCCs were histologically typed as keratinizing (K SCC), nonkeratinizing (NK SCC), and nonkeratinizing with maturation (NK SCC with maturation), as previously described by Chernock et al. 2009, Head Neck Pathol 3: 186-194, and Lewis et al 2010, Am J Surg Pathol 34: 1088-1096.
[b]Smoking was defined as any lifetime smoking use versus no history of smoking.

For all the patients, formalin-fixed, paraffin-embedded (FFPE) tumor tissues were collected for pathological analysis before radiotherapy or chemotherapy. Sections from each case were stained with hematoxylin and eosin and reviewed independently by two study pathologists to confirm the diagnoses. Tumor regions from each section were identified and macrodissection was performed. Finally, total RNA was extracted from the identified tumor regions with the miRNeasy FFPE Kit (Qiagen Inc, Valencia, Calif.) according to the manufacturer's protocol. In this way, it was possible to focus on the profiling of the tumor tissues with minimal contamination from adjacent normal tissues.

miRNA and HPV Expression Profiling miRNA expression profiling was performed using a method recently developed by the inventors, which is based on real-time reverse transcriptase-polymerase chain reaction (RT-PCR; Wang 2009, RNA 15:716-723). The details of the experimental procedure were as described previously. In brief, the RT reaction was performed with the High Capacity cDNA Reverse Transcription Kit (Applied Biosystems, Foster City, Calif.). Each RT reaction included 150 ng of tumor RNA and a pool of miRNA-specific RT primers. Real-time PCR was performed with Power SYBR Green PCR Master Mix (Applied Biosystems) and miRNA-specific PCR primers. Raw profiling data based on PCR threshold cycles (Ct) were normalized using a quantile-based scaling method as described previously.

The expression profiles of E6 and E7 from oncogenic HPV types were also determined by real-time RT-PCR. New HPV assays were designed based on an algorithm previously developed by the inventors (Wang and Seed 2003, Nucleic Acids Res 31:e154), and the details of the new design are described elsewhere (Gao et al. 2013 Int J Cancer 132:882-90). In brief, primer sequences were selected from the E6 and E7 coding regions of the high-risk HPV types 16, 18, 31, 33, 35, 39, 45, 52, 56, 58, 59, 66, and 68. The expression profiles of glyceraldehyde 3-phosphate dehydrogenase (GAPDH) and β-actin were used as reference controls for data normalization.

Survival Analysis

Overall survival (OS) and disease-specific survival (DSS) were used as the endpoints to represent disease outcome, defined as the time interval between treatment start date and the date of death from any cause (OS) or the date of death with cancer disease (DSS). Statistical data analyses were performed using the R statistical package (www.r-project.org/). Univariate Cox proportional hazards regression analyses were performed to evaluate the correlation between miRNA or HPV signatures with disease outcome. The P values for outcome correlation were calculated using the Wald test, and further adjusted by permutation tests as previously described. Multivariate Cox proportional hazards regression analyses were performed to evaluate the independent prognostic value of the miRNA signature after controlling for common clinical variables. Residuals from Cox models were examined graphically and tested for proportional hazards assumption. The Kaplan-Meier estimator was used to estimate the empirical survival probabilities, and P values from the log-rank test indicated the significance of the miRNA outcome prediction model.

Example 1 miRNA Expression Profile was Correlated with Oropharyngeal Cancer Survival miRNA expression profiling was performed for 101 oropharyngeal SCC cases in the training cohort. The characteristics of these patients are summarized in Table 1. Total RNA extracted from the tumor tissues was profiled using real-time PCR-based assays for 96 cancer-related miRNAs previously established by the inventors (Wang 2009, RNA 15:716-723). PCR-based profiling assays for all these miRNAs had been designed and validated experimentally (Wang 2009, RNA 15:716-723).

The miRNA profiling data were analyzed to identify individual miRNAs that were correlated with disease outcome using univariate Cox proportional hazards regression models. Among all the miRNAs included in the profiling study, 13 were found to be significantly correlated with OS (Table 2). The independent prognostic values of these candidate miRNAs were evaluated further by controlling for treatment protocols (chemotherapy and radiotherapy status) and disease stage with multivariate Cox regression analysis. Six miRNAs, including miR-142-3p, miR-31, miR-146a, miR-26b, miR-24, and miR-193b, retained their prognostic significance in this multivariate analysis and thus were selected for further model development.

TABLE 2 miRNAs correlated with overall survival[a]

| miRNA Name | P | Fold Change |
|---|---|---|
| miR-142-3p | .00079 | −0.54 |
| miR-31 | .0015 | 1.14 |
| miR-146a | .0050 | −0.34 |
| miR-26b | .0081 | −0.25 |
| miR-24 | .0091 | 0.15 |
| miR-29b | .0098 | −0.30 |
| miR-203 | .012 | 0.61 |
| miR-155 | .014 | −0.41 |
| miR-193b | .015 | 0.48 |
| miR-26a | .019 | −0.29 |
| miR-215 | .020 | 0.34 |

TABLE 2-continued miRNAs correlated with overall survival[a]

| miRNA Name | P | Fold Change |
|---|---|---|
| miR-101 | .029 | −0.26 |
| let-7i | .044 | −0.11 |

Abbreviation:
miRNA, microRNA.

[a]The P values were calculated using the Wald test in univariate Cox regression analysis, and were adjusted further with permutation tests. The fold change values were $log_2$ transformed, representing the average expression difference of the miRNAs in 2 patient groups (deceased vs. alive).

To more closely examine the expression profiles of these selected miRNAs in relation to patient survival, the 101 patients were stratified into two groups based on survival outcome (deceased vs alive). The expression profiles of these six miRNAs in the two patient groups are shown in FIG. 1. It is interesting to note that three miRNAs (miR-142-3p, miR-146a, and miR-26b) were preferentially overexpressed in the surviving patients, whereas the remaining miRNAs (miR-31, miR-24, and miR-193b) were overexpressed in the patients who died.

Example 2

A miRNA Signature to Predict Cancer Survival

Given the significant correlation between miRNA expression and patient survival, it was hypothesized that a combined expression signature of multiple miRNAs may be used for outcome prediction. Thus, the six miRNAs selected from the profiling studies were used to build a prognostic model to predict OS as follows:

$$S = 2.62 E_{miR-24} + 3.16 E_{miR-31} + 2.45 E_{miR-193b} - 2.69 E_{miR-26b} - 3.34 E_{miR-142-3p} - 2.81 E_{miR-146a}$$

in which S represents the risk score for each patient and E represents the normalized expression level of individual miRNAs from each tumor. The coefficient for each miRNA in this equation is the Z score from the Cox regression analysis, defined as Z=(Cox regression coefficient)/(standard error of the coefficient).

Figure 2:
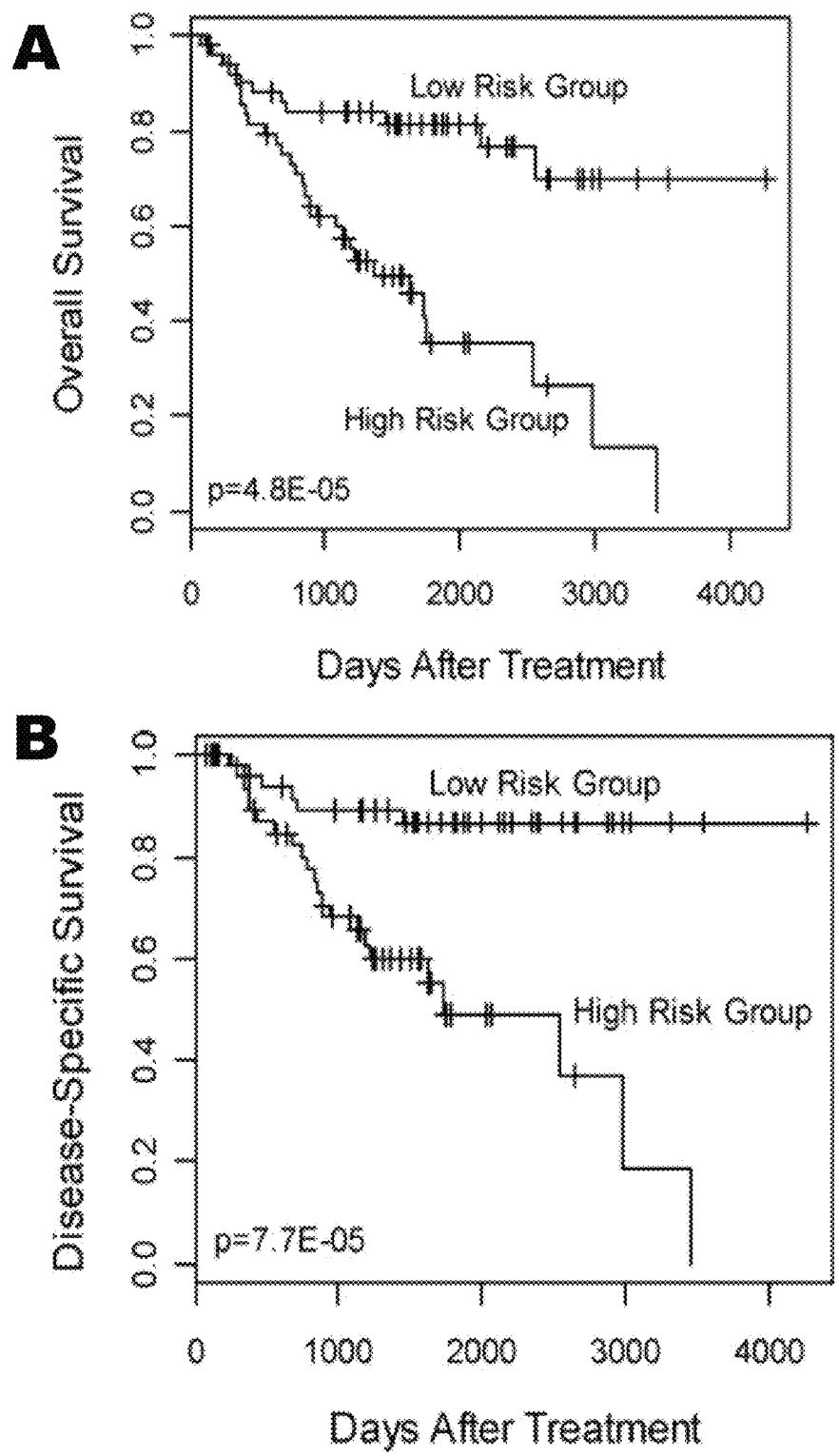
FIG. 2 depicts four plots showing Kaplan-Meier survival analysis of miRNA. Kaplan-Meier survival analysis was used to evaluate the microRNA (miRNA) signature using the training cohort. A risk score was calculated based on the final miRNA prediction model and assigned to each patient. Based on the risk score, the patients were stratified into either the low-risk group or the high-risk group. The prognostic value of the miRNA risk scores was evaluated with regard to (A) overall survival and (B) disease-specific survival. The P values were calculated using the log-rank test. (C and D) Leave-one-out cross-validation was used to evaluate the miRNA modeling strategy. The cross-validated results from all 101 rounds were combined for prognostic evaluation using (C) overall survival and (D) disease-specific survival.
Figure 2:
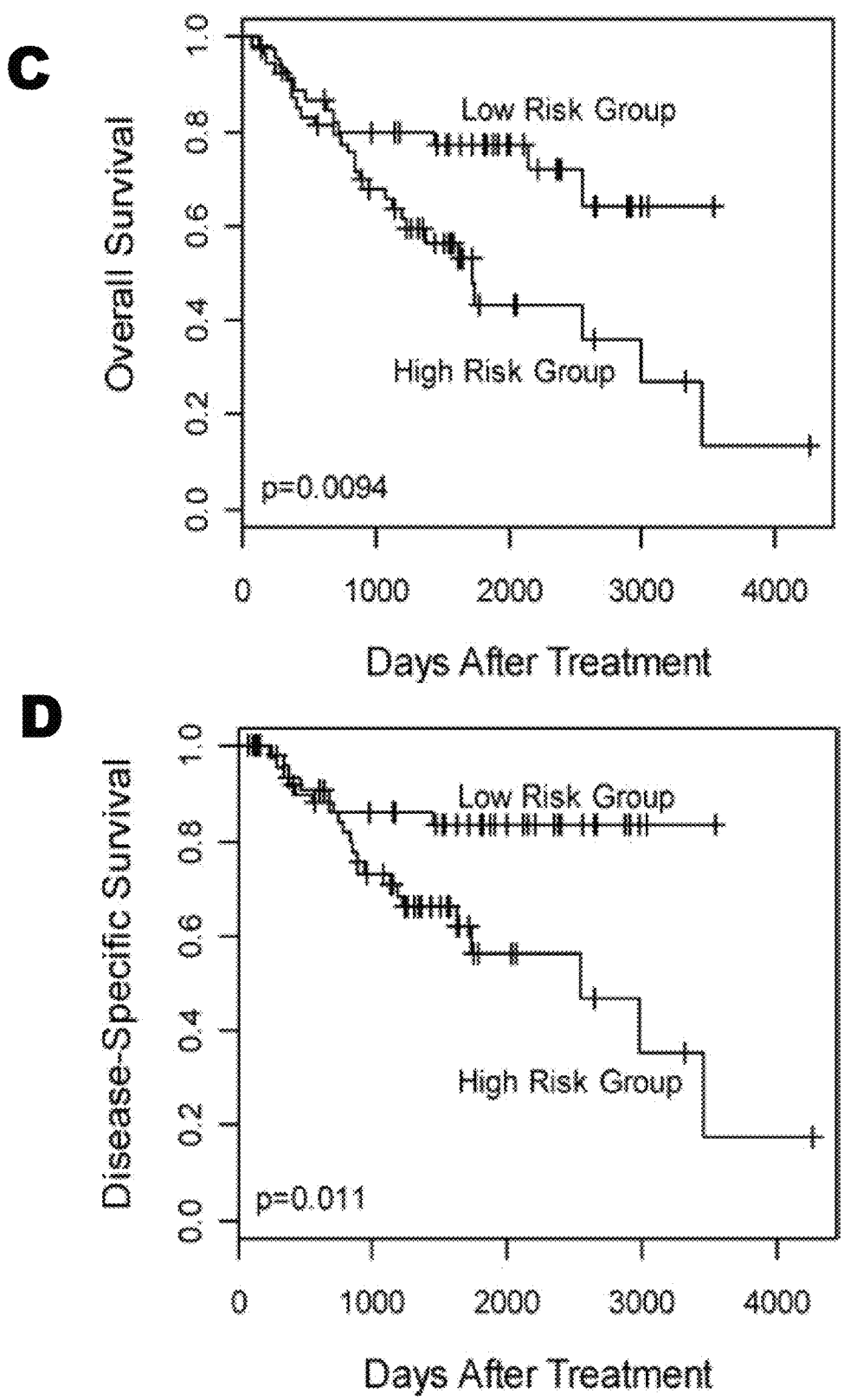

In this prediction model, a high-risk score predicts poor survival for the patient. By the median risk score, the 101 patients were divided into 2 cohorts of similar size. In this way, 51 patients were predicted to be of high risk (with ≥ the median score) and 50 to be of low risk (with < the median score). Kaplan-Meier survival analysis indicated that the 2 cohorts exhibited distinct risks for death (P=4.8E-05) (FIG. 2A). Similarly, the miRNA risk score was also found to be significantly prognostic of DSS (P=7.7E-05) (FIG. 2B).

One common issue in computational modeling is the risk of overtraining (i.e., the model may work well with the training data, but not with independent testing data). To evaluate the potential risk of overtraining from our modeling strategy, leave-1-out cross-validation was performed. In this cross-validation analysis, for each round, miRNA profiles from 100 training tumors were used to build a prediction model and the 1 remaining tumor was reserved for independent model testing. The process was rotated 101 rounds until all the tumors had been used for model testing. For each validation round, candidate miRNAs were selected based on their prognostic significance for OS of the training tumors as well as independence from treatment protocols and disease stage, using the same miRNA selection strategy as described earlier. Similarly, a prediction model was built in each validation round by combining the selected miRNAs, using the Z score for each miRNA as the coefficient in the model (details described earlier). The median score from each model was used to classify the reserved independent testing case. In this way, 101 slightly different models (from the final model) were developed and tested, and the crossvalidated results from all 101 rounds were combined for performance evaluation. The cross-validated data were prognostic of both OS (FIG. 2C) and DSS (FIG. 2D), demonstrating the robustness of our computational modeling strategy.

Example 3

Correlation of miRNA Expression with HPV Expression

Unlike most other types of head and neck cancer, previous studies have indicated that oropharyngeal cancer is strongly correlated with HPV infection. To comprehensively analyze the expression profile of HPV in oropharyngeal cancer, a new real-time RTPCR method was developed by the inventors to quantify the transcriptional activity of E6 and E7 genes from 13 oncogenic HPV types (Wang 2009, RNA 15:716-723). With this new method, HPV E6 and E7 transcripts were detected in 82 of the 101 cancer patients, including 75 cases of HPV-16, 6 cases of HPV-33, and 1 case of HPV-35.

The prognostic significance of HPV detection in patients with oropharyngeal SCC was evaluated using univariate Cox regression analysis. Both the status of the HPV detection (present or absent) and the expression level of HPV (averaged E6 and E7 expression) were evaluated. Both HPV status and HPV expression level were found to be significantly correlated with OS (P=0.017 and P=0.034, respectively). Thus, consistent with previous studies, HPV infection was a prognostic marker for oropharyngeal SCC. To determine whether the inclusion of HPV could further enhance the prognostic performance of the miRNA-based prediction model, the miRNA signature and HPV infection were evaluated using multivariate Cox analysis. As a result, HPV status was no longer found to be significant with the incorporation of the miRNA risk score (P=0.49). In contrast, the significance of the miRNA signature was retained (P<0.001). Thus, the prognostic value of the HPV status was already reflected in the miRNA signature, and adding this HPV feature is not likely to further enhance the model performance.

Figure 3:
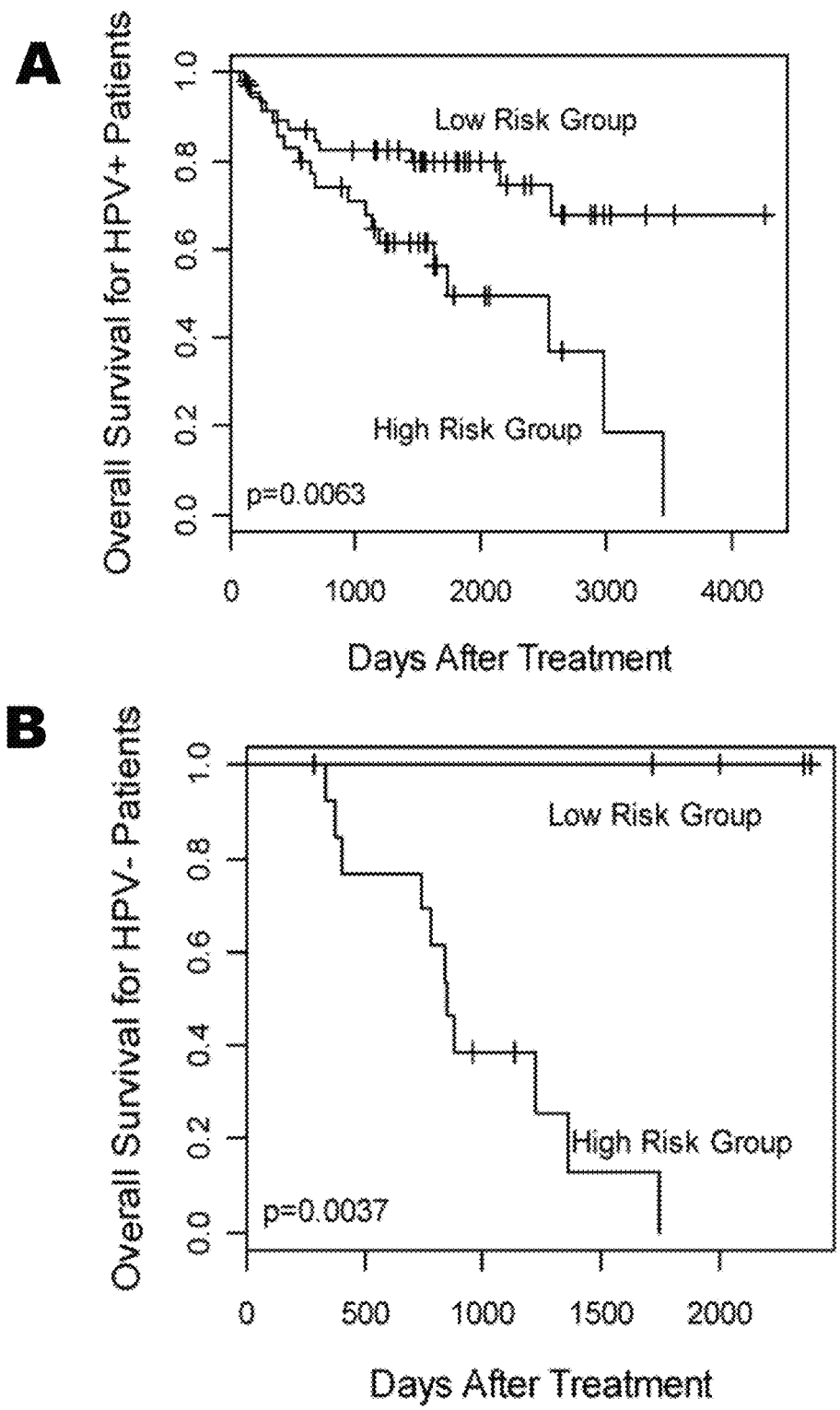
FIG. 3 depicts two plots showing Kaplan-Meier survival analysis of miRNA. Kaplan-Meier survival analysis was used to evaluate the independence of the microRNA (miRNA) signature from human papillomavirus (HPV) infection. The patients were stratified into two groups based on their HPV status. The miRNA model was applied to (A) patients who were HPV positive (HPV+) or (B) patients who were HPV negative (HPV−) separately.

To further examine the impact of HPV infection on miRNA model performance, patients were stratified into two groups according to their HPV status (HPV positive vs HPV negative). The miRNA model was applied separately to the prognosis of these 2 patient groups. Survival analysis indicated that the miRNA signature was prognostic for both groups, with P values of 0.0063 and 0.0037 for HPV-positive and HPV-negative patients, respectively (FIG. 3). Thus, the prognostic performance of the miRNA signature was independent of the HPV status.

Individual miRNA expression profiles were also found to be correlated with HPV status. Student t tests were performed to evaluate miRNA expression differences between the HPV-negative and HPV-positive patients. Among all the miRNAs analyzed, 5 were found to be significantly correlated with HPV status (miR-9, miR-223, miR-31, miR-18a, and miR-155) (Table 3). It is interesting to note that miR-31 was also included in the miRNA signature, which could help explain why HPV status was not found to be independent of the miRNA signature in the multivariate Cox analysis performed.

TABLE 3 miRNAs correlated with HPV status[a]

| miRNA Name | Fold Change | P |
|---|---|---|
| miR-9 | 1.98 | 1.7E−05 |
| miR-31 | −1.73 | 1.7E−03 |
| miR-223 | −0.98 | 8.6E−04 |
| miR-155 | 0.80 | 3.8E−02 |
| miR-18a | −0.52 | 3.0E−02 |

Abbreviation:
miRNA, microRNA.
[a]The fold change values were log$_2$ transformed. The P values determined by the Student t test were adjusted further for multiple testing using the false discovery rate approach.

Example 4

The miRNA Signature was Independent of Clinicopathologic Features

In this Example, it was assessed whether the new miRNA signature had independent prognostic value within the context of commonly used clinical parameters, including age at diagnosis, sex, race, smoking history, histologic type, stage, radiotherapy status, and chemotherapy status. The prognostic significance of the miRNA signature was evaluated for OS after controlling for the clinical features in a multivariate Cox regression model. The miRNA signature was still found to be statistically significant on this multivariate survival analysis, with a hazard ratio of 3.22 and P=0.0022 (Table 4). Thus, the prognostic significance of the miRNA signature was independent of the clinical features.

TABLE 4

Cox regression analysis to evaluate the independent prognostic value of the miRNA signature and clinical parameters

| Parameter | HR | P[a] |
|---|---|---|
| miRNA signature (high- vs low-risk score) | 3.22 | .0022 |
| Age at diagnosis | 1.00 | .94 |
| Sex (male vs female) | 1.18 | .77 |
| Race (white vs others) | 1.44 | .46 |
| Smoking status (yes vs no) | 1.50 | .39 |
| Histologic type (NK vs K/hybrid) | 1.01 | .98 |
| Stage (I/II/III vs IV) | 1.15 | .77 |
| Radiotherapy status (definitive vs postoperative) | 1.70 | .19 |
| Chemotherapy status (yes vs no) | 1.31 | .47 |

Abbreviations:
HR, hazards ratio;
K, keratinizing;
miRNA, microRNA;
NK, nonkeratinizing.
[a]P values were calculated using the Wald test.

Example 5

Validation of the miRNA Signature with an Independent Cohort

Figure 4:
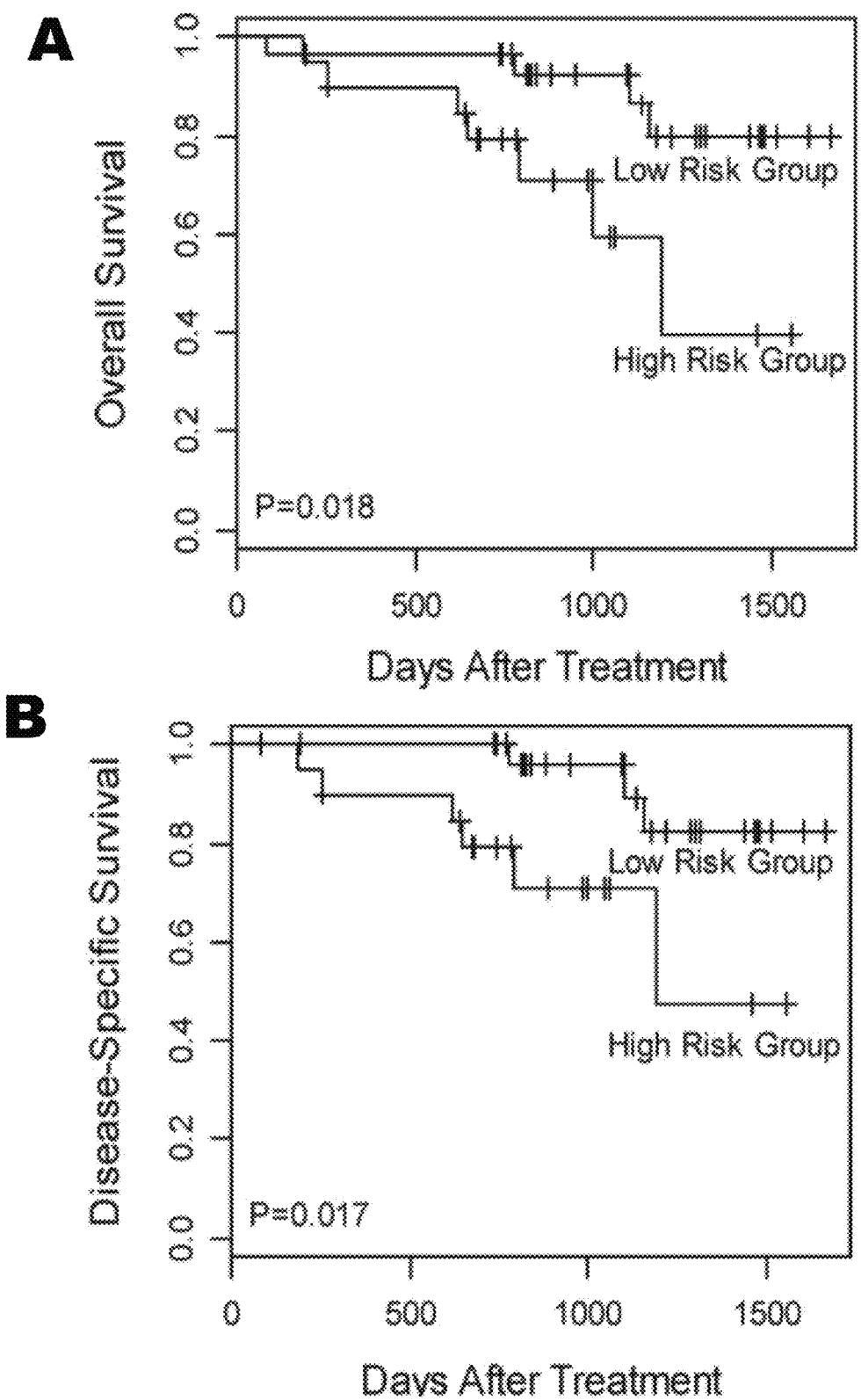
FIG. 4 depicts two plots showing Kaplan-Meier survival analysis of miRNA. Kaplan-Meier survival analysis was used to evaluate the microRNA signature using the validation cohort for (A) overall survival and (B) disease-specific survival.

The miRNA-based prognostic model was validated further with 49 independent cases in a validation cohort (Table 1). First, miRNA expression profiles in the 49 patients were determined by real-time RT-PCR and applied to the miRNA prognostic model. As a result, a risk score was calculated by the prediction model and assigned to each of the 49 patients in the validation cohort. In this way, the patients in the validation cohort were stratified into either the high-risk group (20 patients) or the low-risk group (29 patients) based on the same threshold risk score determined by the training cohort. Kaplan-Meier survival analysis indicated the two patient groups had significantly different OS rates (P=0.018) (FIG. 4A). Similarly, these two patient groups had significantly different DSS rates (P=0.017) (FIG. 4B). Thus, the new miRNA model retained its prognostic significance when applied to an independent patient cohort.

Discussion for Examples 1-5

One major challenge in miRNA expression profile studies is the lack of high-quality tumor tissues for expression analysis. Typically, miRNA expression profiling is performed using freshly frozen tumors for the extraction of high quality RNA. However, the majority of tumors are routinely preserved with FFPE, leading to highly degraded RNA in the archived tumors. Given exclusive focus of this study on oropharyngeal SCC, it was challenging to collect a large number of frozen tumors for miRNA profiling analysis. Instead, archived FFPE tumor tissues that were collected following standard clinical practice were used. To address the challenge of analyzing low-quality RNA, a new PCR-based profiling method for miRNA expression analysis was developed that has robust performance in detection sensitivity and specificity, even when applied to FFPE tumors. In the current study, this new method was applied to the profiling of 150 archived oropharyngeal tumors, resulting in an experimentally validated miRNA signature for the prognosis of oropharyngeal SCC.

As the first step, 101 tumors were analyzed for the development of a miRNA-based prognostic model. The robustness of the modeling strategy has been demonstrated by cross-validation using the same training tumors as well as in a multivariate analysis to control for clinical features. More importantly, the model also has been validated in a separate experiment using a patient cohort comprised of 49 independent cases. The miRNA model was demonstrated to also be useful for prognosticating the validation cohort, which indicated the general applicability of the model. The robust performance of the miRNA model reflected the independent prognostic value of the miRNAs included in the model because these miRNAs were selected based on their prognostic significance as well as independence from common clinical features. Thus, the miRNA signature represents a new expression profile-based strategy for the identification of patients with high-risk oropharyngeal SCC who could benefit from improved treatment strategies.

Among the miRNAs in the prognostic model, miR-31 has been previously shown to be significantly upregulated in patients with head and neck cancer and to play an oncogenic role in oral carcinogenesis. miR-24 also is upregulated in patients with head and neck cancer, leading to enhanced cancer cell proliferation and reduced apoptosis. Consistent with these studies, the present examples demonstrate that both miR-31 and miR-24 were associated with poor prognosis in patients with oropharyngeal SCC. Conversely, miR-146a functions as a tumor suppressor in many cancer types. Consistent with these findings, the present examples demonstrate that miR-146a was associated with a favorable prognosis. Thus, the prognostic value of the miRNAs in the model could result from the functional roles of these miRNAs in oropharyngeal SCC.

Consistent with previous studies, the current profiling analysis also identified HPV as a prognostic marker for oropharyngeal SCC. It is important to note that the current profiling further demonstrated that the new miRNA signature was even more significant than HPV at prognosticating oropharyngeal SCC. Given the important role of HPV infection in oropharyngeal tumor initiation, it is interesting to note that the current study identified five miRNAs that are correlated with HPV transcriptional activity (Table 3). In particular, one such HPV-correlated miRNA, miR-31, also was found to be of prognostic value in patients with oropharyngeal SCC. Another miRNA, miR-9, was found to be a prognostic marker for cervical cancer, as revealed in a study by the inventors (Hu et al. 2010, Cancer Res 70:1441-1448). Because the majority of cervical cancers are caused by HPV infection, the prognostic value of miR-9 in patients with cervical cancer is likely the result of its strong association with HPV infection. These HPV-related miRNAs may help to elucidate the molecular mechanisms as well as identify novel therapeutic targets for HPV-induced cancers, including both oropharyngeal and cervical cancers.

Example 6

Enrollment of Oropharyngeal Cancer Patients

Fifty oropharyngeal squamous cell carcinoma (OPSC) patients may be enrolled in this study. At least 50 oropharyngeal tumors may be collected using an IRB protocol established by the inventors. To date, freshly-frozen tumors from about 130 cancer cases, including 30% of OPSCC cases, were collected by the inventors. Tissue QA on six tumor samples showed high quality of these tumors for a variety of downstream applications, including high-throughput RNA and genomic DNA sequencing, as well as sensitive detection of HPV infection, which highlights the robustness of the procedures. For each consented patient, fresh oropharyngeal tumor biopsies may be collected. For an aliquot of each biopsy, total RNA extraction may be extracted and analyzed for validation of the prognostic miRNA signature.

Fifty oropharyngeal tumor samples may be analyzed for the validation of the panel of prognostic miRNAs described in Examples 1-5. In this study, it may be determined if there exists a significant association between patients classified as high-risk via the miRNA model and cancer-specific survival rates at 5 years. Therefore, if current estimates are used about the incidence of high-risk patients (approximately 50%) and 5-year survival estimates of 50% and 90% for high-risk and low-risk patients, respectively, the current study may provide 89% power to detect a significant difference association between risk group and 5-year survival at the 5% significance level.

Example 7

Validation of the Prognostic miRNA Panel with a Prospective Patient Cohort

To further demonstrate the clinical relevance of the panel of prognostic miRNAs identified in Examples 1-5, the miRNA signature may be validated using prospectively-collected independent oropharyngeal tumor samples described in Example 6. The confirmation of these prognostic miRNAs in prospective tumor samples may lay a solid foundation for future clinical trials on evaluating the effectiveness of using the miRNA model to identify high-risk oropharyngeal cancer patients in clinical settings.

The panel of prognostic miRNAs may be validated with 50 prospectively collected oropharyngeal cancers. Total RNA may be extracted from the tumor tissues and real-time RT-PCR experiments may be performed to determine the expression of the prognostic miRNAs using the same method as described in Wang and Seed 2003, Nucleic Acids Res 31:e154. A risk score may be calculated for each patient based on the miRNA predictive model as described in Example 2.

Overall survival (OS) and metastasis-specific survival (DSS) may be used as the end points to represent disease outcome, defined as the time interval between treatment start date and the date of death from any cause (OS) or the date of death with metastatic disease (DSS). Outcome data may be collected for the following three years to continue follow up of the cancer patients. Based on clinical data analysis, most (>90%) oropharyngeal cancer distant metastases for surgically treated patients occurred within two years, and local recurrences within a year. Thus, a conservative three-year outcome data may be used for an initial evaluation of the miRNA signature. Five-year follow-up data may also be used later for a more complete assessment of the miRNA signature.

Logistic regression may be used to correlate the miRNA predictive model result with the survival endpoint while ROC curve analysis may be applied to report sensitivity, specificity, positive and negative predictive values. Furthermore, Kaplan-Meier product limit method with log-rank test and Cox proportional hazard model may be conducted.

What is claimed is:

1. A method of identifying a subject with oropharyngeal cancer as having a poor or a favorable prognosis, the method comprising:
    (a) obtaining a tissue sample yielding low quality RNA from a subject;
    (b) using a PCR-based profiling method for miRNA expression, to determine in the sample, the levels of six prognostic miRNAs selected from the group consisting of miR-142-3p, miR-31, miR-146a, miR-26b, miR-24, and miR-193b;
    (c) calculating a risk score using the levels of miRNAs determined, and
    (d) comparing the risk score to a median risk score,
    wherein, if (i) the risk score is equal to or higher than the median risk score, the subject has a poor prognosis, and (ii) the risk score is lower than the median risk score, the subject has a favorable prognosis, wherein poor prognosis is indicative of a significantly greater risk of death.

2. The method of claim 1, wherein the sample is processed by real time PCR.

3. The method of claim 2, wherein the real time PCR is preceded by reverse transcription of each miRNA into a cDNA using reverse transcription primers specific for each miRNA.

4. The method of claim 3, wherein each reverse transcription primer specific for each miRNA comprises bases that anneal to the 3' end of the mature miRNA sequence and a unique tag sequence.

5. The method of claim 4, wherein the reverse transcription of the prognostic miRNAs is performed in a multiplexed reaction.

6. The method of claim 2, wherein the real time PCR for each miRNA is performed individually.

7. The method of claim 6, wherein each real time PCR is performed using two PCR primers, wherein the first PCR primer anneals to the unique tag sequence of the reverse transcription primer, and the second PCR primer anneals to a unique sequence in the reverse transcribed sequence of the miRNA.

8. The method of claim 1, wherein the median risk score is calculated from the risk score of a population of subjects with oropharyngeal squamous cell carcinoma.

9. A method for determining the prognosis of a subject with oropharyngeal carcinoma, the method comprising:
(a) obtaining a tissue sample yielding low quality RNA from a subject;
(b) using a PCR-based profiling method for miRNA expression, to determine in the sample, the levels of six prognostic miRNAs selected from the group consisting of miR-142-3p, miR-31, miR-146a, miR-26b, miR-24, and miR-193b;
(c) calculating a risk score (S) according to the following formula:

$$S=C_1E_1+C_2E_2+C_3E_3-C_4E_4-C_5E_5-C_6E_6, \text{ wherein:}$$

$C_1$, $C_2$, $C_3$, $C_4$, $C_5$, and $C_6$ are coefficients;
$E_1$ is the expression level of miR-24;
$E_2$ is the expression level of miR-31;
$E_3$ is the expression level of miR-193b;
$E_4$ is the expression level of miR-26b;
$E_5$ is the expression level of miR-142-3p;
$E_6$ is the expression level of miR-146a; and
assessing prognosis by comparing the risk score to a median risk score, wherein, if (i) the risk score is equal to or higher than the median risk score, the subject has a poor prognosis, and (ii) the risk score is lower than the median risk score, the subject has a favorable prognosis, wherein poor prognosis is indicative of a significantly greater risk of death.

10. The method of claim 9, wherein the method further comprises measuring expression level of at least one miRNA selected from the group consisting of miR-29b, miR-203, miR-155, miR-26a, miR-215, miR-101, and let-7i.

11. The method of claim 9, wherein the median risk score is calculated from a population of subjects having oropharyngeal carcinoma.

12. The method of claim 9, wherein each of $C_1$, $C_2$, $C_3$, $C_4$, $C_5$, and $C_6$ is a Cox regression analysis Z score.

13. The method of claim 12, wherein the Z score is equal to Cox regression coefficient/standard error of the coefficient.

14. The method of claim 9, wherein the expression level of each miRNA is a normalized level of expression.

15. The method of claim 9, wherein the oropharyngeal carcinoma is a squamous cell carcinoma.

16. The method of claim 1, wherein the method further comprises determining in the sample the levels of at least one prognostic miRNA selected from the group consisting of miR-29b, miR-203, miR-155, miR-26a, miR-215, miR-101, and let-7i.

17. The method of claim 1, wherein the tissue sample yielding low-quality RNA is a formalin-fixed paraffin-embedded (FFPE) tissue sample.

18. The method of claim 9, wherein the tissue sample yielding low-quality RNA is a formalin-fixed paraffin-embedded (FFPE) tissue sample.

* * * * *